US010940206B2

(12) United States Patent
Claret et al.

(10) Patent No.: US 10,940,206 B2
(45) Date of Patent: *Mar. 9, 2021

(54) OPHTHALMIC COMPOSITION COMPRISING LIPOIC ACID AND A MUCOMIMETIC POLYMER

(71) Applicant: OPHTALMIS MONACO, Monaco (MC)

(72) Inventors: Martine Claret, Saint Sulpice (CH); Claude Claret, Saint Sulpice (CH); Caroline Chatard-Baptiste, Nice (FR)

(73) Assignee: OPHTALMIS MONACO, Monaco (MC)

( * ) Notice: Subject to any disclaimer, the term of this patent is extended or adjusted under 35 U.S.C. 154(b) by 0 days.

This patent is subject to a terminal disclaimer.

(21) Appl. No.: 15/575,200

(22) PCT Filed: May 20, 2016

(86) PCT No.: PCT/EP2016/061362
§ 371 (c)(1),
(2) Date: Nov. 17, 2017

(87) PCT Pub. No.: WO2016/185000
PCT Pub. Date: Nov. 24, 2016

(65) Prior Publication Data
US 2018/0147283 A1    May 31, 2018

(30) Foreign Application Priority Data

May 21, 2015 (FR) ...................................... 1554590
Mar. 11, 2016 (FR) ...................................... 1652042

(51) Int. Cl.
| A61K 47/22 | (2006.01) |
| A61K 31/728 | (2006.01) |
| A61K 9/00 | (2006.01) |
| A61K 9/107 | (2006.01) |
| A61P 27/02 | (2006.01) |
| A61K 31/385 | (2006.01) |
| A61K 45/06 | (2006.01) |

(52) U.S. Cl.
CPC ............ *A61K 47/22* (2013.01); *A61K 9/0048* (2013.01); *A61K 9/107* (2013.01); *A61K 31/385* (2013.01); *A61K 31/728* (2013.01); *A61K 45/06* (2013.01); *A61P 27/02* (2018.01)

(58) Field of Classification Search
CPC ...... A61K 47/22; A61K 9/107; A61K 9/0048; A61K 31/728; A61P 27/02

USPC ........................................................... 514/54
See application file for complete search history.

(56) References Cited

U.S. PATENT DOCUMENTS

| 5,817,630 | A | 10/1998 | Hofmann et al. |
| 6,162,393 | A | 12/2000 | De Bruiju et al. |
| 6,620,425 | B1 | 9/2003 | Gardiner |
| 6,649,195 | B1 | 11/2003 | Gorsek |
| 2001/0031744 | A1 | 10/2001 | Kosbab |
| 2004/0265345 | A1 | 12/2004 | Perricone |
| 2005/0192229 | A1 | 9/2005 | Perricone |
| 2006/0127505 | A1 | 6/2006 | Haines et al. |
| 2006/0188492 | A1 | 8/2006 | Richardson |
| 2006/0216251 | A1 | 9/2006 | Morariu |
| 2007/0207116 | A1 | 9/2007 | Brown |
| 2010/0317608 | A1* | 12/2010 | Garner ................. A61K 9/0048 514/42 |
| 2012/0258168 | A1 | 10/2012 | Montesinos |

FOREIGN PATENT DOCUMENTS

| CN | 102144780 A | 8/2011 |
| CN | 103860625 A | 6/2014 |
| DE | 10229995 A1 | 1/2004 |
| EP | 2311454 A2 | 4/2011 |
| JP | 2013241398 A | 12/2013 |
| WO | 0193824 A1 | 12/2001 |
| WO | 02098345 A1 | 12/2002 |
| WO | 2005027950 A1 | 3/2005 |
| WO | 2006128618 A1 | 12/2006 |
| WO | 2009080220 A1 | 7/2009 |
| WO | 2011131765 A2 | 10/2011 |
| WO | 2012013736 A1 | 2/2012 |
| WO | WO2015/057751 * | 4/2015 |
| WO | 2015150459 A1 | 8/2015 |

OTHER PUBLICATIONS

Kofuji et al., "Stabilization of a-lipoic acid by complex formation with chitosan" Food Chemistry—Dec. 2007, vol. 109: 167-171.
Masami Kojima et al., "Efficacy of a-Lipoic Acid Against Diabetic Cataract in Rat" Japanese Journal of Ophthalmology, Jan. 2007, vol. 51, Issue 1, pp. 10-13.
International Search Reported in Corresponding Application No. PCT/EP2016/061362 dated Jul. 18, 2016.

* cited by examiner

*Primary Examiner* — Yih-Horng Shiao
(74) *Attorney, Agent, or Firm* — McBee Moore & Vanik IP, LLC

(57) ABSTRACT

The present invention relates to an ophthalmic composition in the form of an oil-in-water emulsion comprising a mucomimetic polymer and lipoic acid as emulsion stabilizer. It also relates to a process for stabilizing emulsions with lipoic acid and to the use of this acid for stabilizing the oil-in-water emulsions comprising a mucomimetic polymer.

20 Claims, No Drawings

OPHTHALMIC COMPOSITION COMPRISING LIPOIC ACID AND A MUCOMIMETIC POLYMER

CROSS-REFERENCE TO RELATED APPLICATIONS

This application is a National Stage entry of International Application No. PCT/EP2016/061362, filed May 20, 2016, which claims priority to French Patent Application No. 1554590, filed May 21, 2015, and French Patent Application 1652042, filed Mar. 11, 2016.

BACKGROUND

Field of the Invention

The present invention relates to an ophthalmic composition in the form of an oil-in-water emulsion comprising a mucomimetic polymer and lipoic acid as emulsion stabiliser. It also relates to a process for stabilising emulsions with lipoic acid and to the use of this acid to stabilise oil-in-water emulsions comprising a mucomimetic polymer.

Description of Related Art

Emulsions are known comprising mucomimetic polymers, in particular ophthalmic compositions in the form of said emulsions (WO 2011/131765, WO 2012/013736, WO 2015/150459). Such emulsions however, particularly in the absence of any preserving agent, may exhibit stability problems over time, reducing the homogeneity of the composition and efficient use thereof.

Lipoic acid, also called thioctic acid (CAS n° 0001077-28-7) and the derivatives thereof are known for their antioxidant properties. It is utilised as food supplement in tablet form (Liponsäure-ratiopharm® marketed in Germany by Ratiopharm) or for injection in the form of diluted solutions for injection (Neurium® marketed in Germany by Hexal), optionally to accompany treatments of diabetic patients. Its antimicrobial properties have also been described for use thereof in contact lens cleaning solutions containing BDT (U.S. Pat. No. 6,162,393). The antioxidant properties of lipoic acid have also been highlighted to study its efficacy on diabetic cataracts in rats (Masami Kojima & col., Japanese Journal of Ophthalmology, January 2007, Volume 51, Issue 1, pp 10-13). Ophthalmic or cosmetic compositions able to comprise lipoic acid as antioxidant agent are described in patent applications (US 2006/188492, US 2004/265345, U.S. Pat. No. 5,817,630, WO 02098345, DE10229995, WO 01/93824, US 2005/192229, BR PIO 800 818, CN 103 860 625 et JP 2013 241398).

The inventors have now ascertained that the addition of lipoic acid to an oil-in-water emulsion comprising a mucomimetic polymer is able to improve the stability of the emulsion.

SUMMARY OF THE INVENTION

The present invention relates to an ophthalmic composition in the form of an oil-in-water emulsion comprising a mucomimetic polymer and lipoic acid. The lipoic acid has the effect of stabilising the emulsion.

The invention more particularly concerns an ophthalmic composition in the form of an oil-in-water emulsion comprising hyaluronic acid or salts thereof as mucomimetic polymer, and lipoic acid.

Unless otherwise indicated, the percentages are expressed by weight relative to the total weight of the composition.

The invention also relates to a process for stabilising an oil-in-water emulsion comprising a mucomimetic polymer, comprising the addition of lipoic acid before or during the emulsification step of the composition.

The invention also relates to the use of lipoic acid to stabilise an oil-in-water emulsion comprising a mucomimetic polymer.

DETAILED DESCRIPTION OF A PREFERRED EMBODIMENT

The present invention relates to an ophthalmic composition in the form of an oil-in-water emulsion comprising a mucomimetic polymer and lipoic acid as stabiliser of the emulsion.

By ophthalmic composition according to the invention is meant any composition intended to be applied to the eye or ocular mucosa. Ophthalmic compositions may be viscous compositions such as ointments or creams, or else liquid compositions called eyedrops.

The ophthalmic composition must meet technical characteristics specific to ophthalmic compositions, and more particularly those related to the selection of the components thereof. These components that are "ophthalmically acceptable" must not, either individually or associated within the composition, cause eye side effects other than the effect targeted by the composition and its active ingredients. Since the eye is a particularly sensitive organ to environmental stress, the composition must not cause parasitic irritations or reactions of allergic type detrimental to the intended use, and more particularly ophthalmic compositions intended to treat an eye disorder. The choice of constituents of the composition is therefore of high importance, thereby distinguishing between the ophthalmic composition and a simple composition that is unsuitable for ophthalmic use. It is within the reach of persons skilled in the art to select said components and to differentiate between an ophthalmic composition and a simple composition intended for another use.

The mucomimetic polymers used in the emulsion of the invention are polyosides, particularly selected from among polysaccharides, also known as glycans or polyholosides, and more particularly from among glycosaminoglycans (GAG) and hyaluronic acids. These polymers, also called acid mucopolysaccharides, can be characterized by a strong water-retaining capacity imparting mucomimetic properties thereto.

The mucomimetic polysaccharides of the invention comprise at least 5, particularly at least 10, more particularly at least 20 ose or monosaccharide units. Particular mention is made of dextran sulfate which is a complex polysaccharide in particular of molecular weight ranging from 4 to 500 kDa, arabinogalactan which is a biopolymer composed of monosaccharides of arabinose and galactose, and is a natural constituent of some gums and of the walls of some mycobacterial cells, heparin particularly of molecular weight ranging from 6 to 30 kDa, keratan sulfate, chondroitin sulfate particularly of molecular weight of about 50 kDa, dermatan sulfate and hyaluronic acid which is a disaccharide polymer having high viscosity and naturally present in numerous tissues including conjunctive tissue and one of the chief constituents of the extracellular matrix. This latter polymer can be obtained by extraction from animal tissue or via bacterial fermentation. The mucomimetic polymer is more preferably selected from among glycosaminoglycans, hyaluronic acids and mixtures thereof.

The mucomimetic polymer may have a molecular weight ranging from 10 to 10 000 kDa, particularly 500 to 1 500 kDa, even about 1 000 kDa.

The emulsion of the invention has a content of mucomimetic polymer ranging from 0.01 to 5% by weight relative to the total weight of the composition, in particular ranging from 0.05 to 2.5% by weight, more particularly ranging from 0.1 to 1% by weight, even ranging from 0.15 to 0.5% by weight, and further particularly it is about 0.18% by weight relative to the total weight of the emulsion.

According to one preferred embodiment of the invention, the composition comprises hyaluronic acid or the salts thereof as mucomimetic polymer. The different forms of hyaluronic acid or salts thereof used in pharmaceutical or cosmetic compositions are well known to persons skilled in the art and can be used in the compositions of the invention.

Preferably hyaluronic acid is used in the form of an alkaline metal salt, particularly its sodium salt. Particular mention is made of sodium hyaluronate having an intrinsic viscosity ranging from 1.4 to 2.2 m3/kg.

Preferably, the emulsion of the invention has a content of hyaluronic acid or the salts thereof ranging from 0.05 to 2% by weight relative to the total weight of the composition, in particular ranging from 0.1 to 0.2% by weight.

By lipoic acid according to the invention it is meant to designate 5-(1,2dithiolan-3-yl)pentanoic acid, in racemic form or the enantiomers thereof in any proportion, in particular the R enantiomer, pure or in a mixture where the proportion of R enantiomer is higher than that of the S enantiomer, and the pharmaceutically acceptable salts thereof.

Among the pharmaceutically acceptable salts according to the invention it is advantageously meant the addition salts of lipoic acid with a pharmaceutically acceptable base, whether an organic base particularly comprising an amino group such as ammonia, lysine, arginine and other compounds known in the Pharmacopoeia, or an inorganic pharmaceutically acceptable base such as sodium hydroxide, potassium hydroxide, calcium hydroxide and other inorganic bases known in the Pharmacopeia. Preferably the pharmaceutically acceptable salt is a salt of an alkaline metal (sodium, potassium), of an alkaline-earth metal (calcium, magnesium) or an aluminium ion, more preferably a sodium salt.

According to one preferred embodiment of the invention, the lipoic acid is an R enantiomer salt of lipoic acid, in particular a sodium salt (CAS 176110-81-9) or magnesium salt.

Advantageously, the content of lipoic acid in the emulsion of the invention ranges from 0.01 to 0.02% by weight.

Preferably, the lipoic acid/mucomimetic polymer weight ratio ranges from 0.05 to 0.15.

The composition is an oil-in-water emulsion and comprises the usual constituents of such emulsions such as fats, organic solvents, ionic, zwitterionic or non-ionic surfactants and emulsifying agents. The constituents of emulsions particularly used for application to the skin or mucosa are well known to persons skilled in the art. Particular mention can be made of:

emulsion stabilising agents, in particular stabilising polymers such as polyvinyl alcohol polymers, polysorbates, and of cellulose type in particular methylcellulose, ethylcellulose, hydroxypropylcellulose, carboxymethylcellulose, and mixtures thereof; said stabilising agents can be use in contents ranging from 0.05 to 0.2% by weight relative to the total weight of the composition;

surfactants, particularly polysorbates, polyethylene glycols and derivatives thereof, polyoxyethylene-40stearate, sorbitan esters, polyoxyethylene-polyoxypropylene copolymers, polyvinyl alcohols, polyvinylpyrrolidone polymers, and mixtures thereof; said surfactants can be used in contents ranging from 0.01 to 0.5% by weight relative to the total weight of the composition;

preserving agents, in particular quaternary ammoniums, particularly benzalkonium chloride, alkyldimethylbenzylammonium, cetrimide, cetylpyridinium chloride, benzododecinium bromide, benzethonium chloride, cetalkonium chloride, mercury preserving agents such as phenylmercury nitrate/acetate/borate, thiomersal, alcohol preserving agents such as chlorobutanol, benzyl alcohol, phenylethanol, phenylethyl alcohol, carboxylic acids such as sorbic acid, phenols in particular methyl/propyl paraben, amidines e.g. chlorhexidine digluconate, EDTA, chelating agents potential333ing the efficacy of preserving agents in association with at least preserving agent, and mixtures thereof; said preserving agents can be used in contents ranging from 0.001 to 0.1% by weight relative to the total weight of the composition.

lipids, particularly triglycerides and derivatives thereof such as lipids in the acylglycerol or glyceride class, such as castor, soy, sesame, paraffin, lanolin, vaseline, corn, glycerine oils, or oils of monoglycerides or triglycerides of phospholipid type such as phosphoacylglycerides also called phosphoacylglycerols, phosphosphingolipids, phosphonosphingolipids, phosphoglycolipids, phosphosacharolipids and phosphatidylcholines, and mixtures thereof; these lipids can be used in contents ranging from 0.1 to 1.5% by weight relative to the total weight of the composition;

a buffer to stabilise the pH at an acceptable value for use in the eye, in particular a phosphate, acetate, citrate buffer and mixtures thereof; this buffer can be used in a content ranging from 0.1 to 1.5% by weight relative to the total weight of the composition.

The compositions of the invention may comprise other additives usually used to prepare such formulations, softeners, antioxidants, opacifiers, stabilisers, ionic or non-ionic thickeners, silicones, defoamers, hydrating agents, vitamins, fragrances, preserving agents, fillers, sequestrants, colouring agents, bases or acids needed to regulate pH, or any other ingredient usually used to prepare ophthalmic compositions. The ophthalmic compositions of the invention are prepared using techniques well known to those skilled in the art.

According to one preferred embodiment of the invention, the ophthalmic composition of the invention is a preservative-free composition.

The preserving agents generally used in topical compositions (cosmetic, pharmaceutical, ophthalmic, etc.) to prevent germ contamination are well known to skilled persons such as quaternary ammoniums, in particular benzalkonium chloride, alkyl-dimethyl-benzylammonium, cetrimide, cetylpyridinium chloride, benzododecinium bromide, benzethonium chloride, cetalkonium chloride, mercury preserving agents such as phenylmercury nitrate/acetate/borate, thiomersal, alcohol preserving agents such as chlorobutanol, benzyl alcohol, phenylethanol, phenylethyl alcohol, carboxylic acids such as sorbic acid, phenols, particularly methyl/propyl paraben, amidines e.g. chlorhexidine digluconate and/or chelating agents such as EDTA alone or in association with at least one other preserving agent.

By "preservative-free" according to the invention is meant a composition substantially free of such preserving agents to meet the indication "preservative-free". Its preservative content is 10 ppm or less, more particularly 1 ppm or less, preferably it is 0 ppm, no preservative agent being included in the composition.

In the absence of preserving agents, the composition must be subjected to particular treatment during the preparation and packaging thereof to avoid and prevent contamination with pathogens. These treatments and procedures are well known to those skilled in the art. Thereby, a preservative-free composition of the invention differs from an ordinary composition comprising the same ingredients obtained without taking any special precautions or without describing steps of the process allowing this sterility to be obtained that is characteristic of the compositions of the invention, in particular of the ophthalmic compositions.

The pH of the ophthalmic composition of the invention is between 6 and 7. It therefore generally contains a suitable buffer for ophthalmic use known to skilled persons. Particular mention is made of trisodium citrate dihydrate and citric acid monohydrate used alone or in a mixture.

The ophthalmic composition must also be sterile so as not to produce any pathogens likely to develop and lead to ophthalmic complications. By "sterile" in the present invention is meant the absence of bacteria in the meaning of the European Pharmacopeia, 8th Edition (2014). Preferably, the ophthalmic composition comprising the lipoic acid of the invention is a preservative-free composition.

According to one embodiment of the invention, the ophthalmic composition comprises so-called active compounds such as an osmoprotectant, anti-inflammatory agent and/or antioxidant agent.

Among the osmoprotectants able to be used in the invention, mention is made of glycine, taurine, L-Carnitine, erythritol, trehalose, ectoine, betaine, sarcosine, urea, preferably glycerine or taurine.

Among the agents having anti-inflammatory action that can be used with lipoic acid, mention is made of dexamethasone, flurbiprofen, fluorometholone, salicylic acid, hydrocortisone, triamcinolone, rimexolone, preferably flurbiprofen and dexamethasone.

Among the antioxidant agents able to be used, mention is made of taurine, vitamin E, glutathione, vitamin A, vitamin C, preferably taurine.

The viscosity of the emulsion is advantageously chosen so as to allow the maintaining thereof on the eye, in particular on the cornea, for sufficient time to allow it to act.

The viscosity of the ophthalmic composition preferably ranges from 5 to 100 centipoises. This viscosity is measured in accordance with the recommendations of the European Pharmacopeia 2.2.10, using a rotating viscometer at 25° C., and 100s-1. Other apparatus and methods suitable for measuring the viscosity of solutions are known to those skilled in the art and allow similar results to be obtained.

Advantageously, the emulsion of the invention has low viscosity close to that of water, in particular a dynamic viscosity of $10^{-1}$ Pa·s or lower, in particular ranging from $1.5.10^{-3}$ to $8.10^{-2}$, and most particularly ranging from $3.10^{-3}$ to $6.10^{-2}$ Pa.s.

The viscosity of the ophthalmic composition of the invention is adapted through the addition of "ophthalmically acceptable" viscosity agents. Persons skilled in the art have good knowledge of the viscosity agents able to be used for preparing ophthalmic compositions and the amounts to be used to obtain the desired viscosity. Particular mention is made of hydroxypropylmethylcellulose, hydroxyethylcellulose, carboxymethylcellulose, carbomers, agar gels, polyvinylpyrrolidone and polyvinyl alcohol.

Preferably, the ophthalmic composition of the invention comprises a stabilising polymer of cellulose type, in particular methylcellulose, hydroxypropylmethylcellulose, preferably in a content ranging from 0.05 to 0.5% by weight, advantageously from 0.1 to 0.4% by weight, more advantageously from 0.1 to 0.3% by weight, and in particular it is about 0.15% by weight.

The clarity of the emulsion of the invention is advantageously such as defined in the European Pharmacopeia 7.0, ranging from 0 to 5000 NTU, in particular ranging from 0 to 1000 NTU, and more particularly it is about 200 to 700 NTU, even about 500 NTU.

Preferably, the emulsion of the invention is in eyedrop form. In particular it comprises about 70% by weight of water relative to the total weight of the composition, preferably about 80% water and more preferably at least 95% water.

The ophthalmic compositions of the invention are prepared following usual methods known to those skilled in the art. These methods comprise an emulsification step after mixing the constituents of the composition. It is sometimes possible to prepare the two phases separately, aqueous and lipid, in particular when a particular ingredient must be dissolved in one of the phases before mixing. The invention also concerns a process for preparing an oil-in-water emulsion comprising a mucomimetic polymer, with the addition of lipoic acid before or during the emulsification step of the composition.

The lipoic acid is advantageously added to a lipid phase.

The invention also relates to the use of lipoic acid to stabilise an oil-in-water emulsion comprising a mucomimetic polymer.

EXAMPLES

1. Compositions

The compositions given in the following examples were prepared following usual methods in the technical field. Particular hygienic precautions were taken for the preparation and packaging of the preservative-free compositions to prevent any contamination.

| Emulsion 1 | |
| --- | --- |
| Components | Quantity |
| Sodium hyaluronate | 0.18% |
| Lipoic acid | 0.002% |
| Caprylic/Capric Triglyceride | 0.10% |
| Soy lecithin | 0.10% |
| Sodium carboxymethylcellulose | 0.10% |
| Trisodium citrate dihydrate | 0.41% |
| Citric acid | 0.02% |
| NaOH (1N) | qs pH 6.7 |
| Sodium chloride | qs 150 mOsmol/L |
| Water WFI | qs 100% |

| Emulsion 2 | |
| --- | --- |
| Components | Quantity |
| Sodium hyaluronate | 0.18% |
| Lipoic acid | 0.002% |
| Caprylic/Capric Triglyceride | 0.165% |
| Soy lecithin | 0.035% |
| Hydroxymethylcellulose | 0.10% |
| Trisodium citrate dihydrate | 0.41% |

-continued

Emulsion 2

| Components | Quantity |
|---|---|
| Citric acid | 0.02% |
| NaOH (1N) | qs pH 6.7 |
| Sodium chloride | qs 150 mOsmol/L |
| Water WFI | qs 100% |

2. Stability

First laboratory-tested batches allowed evidencing of the improved stability of the emulsions containing lipoic acid. The stability of the emulsions is particularly represented by particle size. The capacity of an emulsion to maintain particles of small size is a marker of stability. Measurements of particle size were performed on formulas with and without lipoic acid, the other ingredients being identical.

The particles remained smaller in emulsions with lipoic acid than in those without, thereby confirming the improvement in stability through the addition of lipoic acid.

Additional studies are planned over 24 months (tests at 1/3/6/12 months, 18 months and 24 months) at 25, 30 and 40° C.

Observations and measurements are to be conducted on: appearance, particle size, viscosity, pH, osmolality and zeta potential.

The greater stability of the emulsions comprising lipoic acid according to the invention is expected with a reduction in particle size, a zeta potential lower than 50 and greater stability over time.

3. Osmoprotective Activity of Lipoic Acid

A study was carried out to determine the osmoprotective capacity of sodium lipoate (A) during hyperosmolar stress on human conjunctival (WKD) and corneal (HCE) cells.

In a second phase, tests were carried out to compare the effect of lipoic acid, glycerin (B), and taurine (C), individually and when the molecules were combined, on HCE cells under hyperosmolar stress conditions.

The osmoprotective activity of A, then A with B and C, was evaluated by measuring cell viability in particular. To that end, cells were preincubated for 17 h with the test substance(s). Next, the medium was removed and the cells were subjected to hyperosmolar stress by addition of sodium chloride (100 mM NaCl) to the culture medium (M199 for the WKD cells and KSFM for the HCE cells). Cellgrowth control cells were contacted with isotonic medium. Cell viability was analyzed preosmotic stress (0 h) in order to measure the effect of the molecules remaining in contact with the cells during the 17 h of incubation, then at 4 h, 8 h and 24 h post-induction of osmotic stress. The cell viability measurement was carried out via an XTT assay.

Various concentrations of A were tested for the "molecule alone" tests: 0.0005%, 0.001%, 0.005%, 0.01% and 0.05% w/v. For the molecule mixture tests, the following concentrations were tested: for A: 0.001%, 0.005%, and 0.01% w/v; for B: 0.25% w/v; and for C: 0.5% and 1% w/v.

To ensure the validity and the significance of the data, the results obtained were analyzed statistically. The results presented below result from the mean of 3 independent repetitions, carried out on different days.

| Cell viability measurements for various concentrations of lipoic acid (sodium lipoate) | | | | |
|---|---|---|---|---|
| | 0 h | 4 h | 8 h | 24 h |
| At 0.0005% | 99.90% | 62.70% | 38.50% | 18.80% |
| At 0.001% | 98.50% | 69.60% | 42.40% | 18.50% |
| At 0.005% | 102.80% | 109.40% | 76.10% | 12.60% |
| At 0.01% | 98.10% | 119.90% | 82.90% | 8.90% |
| At 0.05% | 56.30% | 46.00% | 27.80% | 2.70% |
| NaCl | 98.80% | 50.70% | 33.50% | 25.80% |
| HIDC | 92.30% | 68.80% | 50.40% | 56.40% |

REFERENCES

BR PIO 800 818
CN 103 860 625
DE10 229 995
JP 2013 241398
U.S. Pat. No. 5,817,630
U.S. Pat. No. 6,162,393
US 2004/265345
US 2005/192229
US 2006/188492
WO 01/93824
WO 02/098345
WO 2011/131765
WO 2012/013736
WO 2015/150459
Masami Kojima & col., Japanese Journal of Ophthalmology, January 2007, Volume 51, Issue 1, pp 10-13

The invention claimed is:

1. An ophthalmic composition in the form of an oil-in-water emulsion wherein said composition comprises a mucomimetic polymer and lipoic acid, wherein the mucomimetic polymer is selected from the group consisting of hyaluronic acid and salts thereof, wherein the lipoic acid/mucomimetic polymer weight ratio ranges from 0.05 to 0.15, wherein the content of the lipoic acid is from 0.001 to 0.02% by weight relative to the total weight of the composition, wherein the lipoic acid improves stability of the emulsion, and wherein the composition further comprises a lipid in an amount of 0.1 to 1.5% by weight.

2. The composition according to claim 1, wherein the mucomimetic polymer is a salt of hyaluronic acid.

3. The composition according to claim 1, wherein the content of the mucomimetic polymer ranges from 0.01 to 5% by weight relative to the total weight of the composition.

4. The composition according to claim 1, wherein the lipoic acid is sodium lipoate.

5. The composition according to claim 1, wherein the content of lipoic acid ranges from 0.01 to 0.02% by weight relative to the total weight of the composition.

6. The composition according to claim 1, wherein said composition has clarity of 5000 NTU or lower.

7. The composition according to claim 6, wherein said composition has clarity of 1000 NTU or lower.

8. The composition according to claim 7, wherein said composition has clarity of about 200 to 700 NTU.

9. The composition according to claim 1, wherein said composition is in the form of eyedrops.

10. The composition according to claim 9, wherein said composition comprises at least 70% by weight of water relative to the total weight of the composition.

11. The composition according to claim 10, wherein said composition comprises at least 80% by weight of water relative to the total weight of the composition.

12. A method for preparing a composition comprising an oil-in-water emulsion comprising a mucomimetic polymer and lipoic acid as defined in claim 1, said method comprising mixing and emulsifying components of the composition, and wherein lipoic acid is added before or during the emulsification of the composition.

13. The composition according to claim 10, wherein said composition comprises at least 95% by weight of water relative to the total weight of the composition.

14. The method according to claim 12, wherein the aqueous phase and the lipid phase of the emulsion are prepared separately before mixing and emulsifying.

15. The method of claim 14, wherein lipoic acid is added to the lipid phase.

16. A method of treating a patient in need of an opthalmic mucomimetic polymer comprising applying the composition of claim 1 to the patient's eye.

17. A method of stabilizing a composition comprising a mucomimetic polymer in a concentration of from 0.01 to 5% by weight relative to the total weight of the composition, wherein the composition is an oil-in-water emulsion, the method comprising adding lipoic acid in a concentration of from 0.001 to 0.02% by weight relative to the total weight of the composition to the mucomimetic polymer, and wherein the composition further comprises a lipid in an amount of 0.1 to 1.5% by weight relative to the total weight of the composition.

18. The composition of claim 1, wherein particle size of the emulsion is smaller than particle size of emulsions without lipoic acid.

19. The composition according to claim 1, wherein the content of mucomimetic polymer ranges from 0.1 to 1% by weight relative to the total weight of the composition.

20. The composition according to claim 1, wherein the content of mucomimetic polymer ranges from 0.1 to 0.2% by weight relative to the total weight of the composition.

* * * * *